United States Patent
Li et al.

(10) Patent No.: US 12,187,693 B2
(45) Date of Patent: Jan. 7, 2025

(54) RAPID SYNTHESIS METHOD FOR BIOMASS-BASED AMINE

(71) Applicant: NANJING AGRICULTURAL UNIVERSITY, Jiangsu (CN)

(72) Inventors: Hu Li, Nanjing (CN); Zhen Fang, Nanjing (CN); Richard Lee Smith, Nanjing (CN)

(73) Assignee: NANJING AGRICULTURAL UNIVERSITY, Jiangsu (CN)

( * ) Notice: Subject to any disclaimer, the term of this patent is extended or adjusted under 35 U.S.C. 154(b) by 973 days.

(21) Appl. No.: 17/266,824

(22) PCT Filed: Jul. 31, 2019

(86) PCT No.: PCT/CN2019/098614
§ 371 (c)(1),
(2) Date: Feb. 8, 2021

(87) PCT Pub. No.: WO2020/029846
PCT Pub. Date: Feb. 13, 2020

(65) Prior Publication Data
US 2021/0347750 A1    Nov. 11, 2021

(30) Foreign Application Priority Data
Aug. 6, 2018    (CN) .......................... 201810885588.1

(51) Int. Cl.
C07D 307/52 (2006.01)
C07C 213/02 (2006.01)
C07C 231/08 (2006.01)

(52) U.S. Cl.
CPC .......... *C07D 307/52* (2013.01); *C07C 213/02* (2013.01); *C07C 231/08* (2013.01)

(58) Field of Classification Search
CPC .. C07D 307/52; C07D 213/02; C07D 231/08; C07C 213/02
See application file for complete search history.

(56) References Cited

U.S. PATENT DOCUMENTS

2009/0143622 A1    6/2009    Bobylev

FOREIGN PATENT DOCUMENTS

CN    109053644 A    12/2018

OTHER PUBLICATIONS

Moore, The Leuckart Reation, Organic Reations, 2011, pp. 301-324. (Year: 2011).*
Loupy, Tetrahedron Letters, 1996, vol. 37(45), 8177-8180. (Year: 1996).*
Kalck et al.; "Tandem hydroaminomethylation reaction to synthesize amines from alkenes;" Chem. Rev.; 2018; pp. 3833-3861; vol. 118.
Jagadeesh et al.; "MOF-derived cobalt nanoparticles catalyze a general synthesis of amines;" Science; 2017; pp. 326-332; vol. 358.
Froidevaux et al.; "Biobased amines: From synthesis to polymers; present and future;" Chem. Rev.; 2016; p. 14181-14224; vol. 116.
Liang et al.; "Production of primary amines by reductive amination of biomass-derived aldehydes/ketones;" Angew. Chem. Int. Ed.; 2017; pp. 3050-3054; vol. 56.
Verduyckt et al.; "Ru-catalyzed hydrogenation-decarbonylation of amino acids to bio-based primary amines;" ACS Sustainable Chem. Eng.; 2017; pp. 3290-3295; vol. 5.
Klinkenberg et al.; "Catalytic organometallic reactions of ammonia;" Angew. Chem. Int. Ed.; 2011; pp. 86-95; vol. 50.
Bipp et al.; "Formamides;" Ullmann's Encyclopedia of Industrial Chemistry; Weinheim: Wiley-VCH; 2005.
Moore; "The Leuckart Reaction;" Organic Reactions; 2011; pp. 301-324.
Loupy et al.; "Towards the Rehabilitation of the Leuckart Reductive Amination Reaction Using Microwave Technology;" Tetrahedron Letters; 1996; pp. 8177-8180; vol. 37, No. 45.
Oct. 29, 2019 Search Report issued in International Patent Application No. PCT/CN2019/098614.

* cited by examiner

*Primary Examiner* — D Margaret M Seaman
(74) *Attorney, Agent, or Firm* — Oliff PLC

(57) ABSTRACT

A rapid synthesis method for a biomass-based amine, including: using formamide as an amine source, formic acid as a hydrogen source, and biomass aldehyde or ketone as a raw material, conduct rapid heating promoting direct addition of formamide and aldehyde or ketone compound through microwave-assisted heating and without a solvent and catalyst, and carrying out formic acid reduction preparing and obtaining a corresponding formamide derivative; selectively converting the formamide derivative under the action of a base into a corresponding primary amine through alcoholysis. The microwave-assisted heating reaction system has a significantly higher catalytic efficiency than a corresponding oil bath system, greatly shortens a reaction time, and significantly improves selectivity, where a conversion rate of a biomass aldehyde or ketone compound may reach at least 99%, and a formamide derivative yield may reach 85-99%; the formamide derivative is synthesized to a primary amine through alcoholysis, where a yield may reach 92-99%.

5 Claims, 2 Drawing Sheets

RAPID SYNTHESIS METHOD FOR BIOMASS-BASED AMINE

BACKGROUND

Technical Field

The present invention relates to a rapid synthesis method for a biomass-based amine, and specifically to a method for preparing primary amine by using formamide as an amine source, using formic acid as a hydrogen source, selectively converting a biomass carbonyl compound (aldehyde or ketone compound) into a formamide derivative through microwave-assisted heating and in the absence of a solvent and an exogenous catalyst, and subsequently removing a formyl group.

Related Art

Because problems, such as resource shortage and environmental deterioration, are increasingly serious, raw materials for industrial production are gradually changing from conventional petro-chemical resources to renewable biomass. As an important class of organic compounds, amines are widely applied to daily necessities and industrial commodities, for example, fine chemicals, medicines, polymers, and function materials[1]. Particularly, in the global top 200 types of best-selling medicines, 80% of medicine molecules contain nitrogen or a nitrogen-containing functional group[2]. Therefore, a series of reactions, for example, reduction and amination of a carbonyl compound, reduction and ammonolysis of sugar, hydrogenation and decarboxylation of amino acid, are developed and applied to synthesis of an amine[3-5]. Even though most of catalytic systems or catalysts can obtain relatively ideal activities, it usually takes a very long reaction time. In addition, on the one hand, raw material costs and preparation prices of metal catalysts that are used are both relatively high. On the other hand, the catalysts are extremely easily inactivated in reaction processes, and selectivity for catalytic synthesis of primary amine is usually relatively poor[2,6]. Therefore, it is particularly necessary to develop an efficient and green catalytic process or system for catalyzing conversion of biomass derivatives, to prepare primary amine.

As a transparent liquid, formamide is miscible with water, and can be used not only as a raw material for pharmaceutical production, but also as a softening agent for extensive use in papermaking, artificial cellulose, and the like[7]. Therefore, formamide reserves are usually relatively large, and market prices are also usually relatively low, which lays a sound foundation of raw materials and markets for developing and utilizing the formamide to prepare a biomass-based primary amine. More importantly, the formamide has a dipole moment and a dielectric constant equivalent to those of water, so that the formamide has a relatively high potential application value in aspects such as microwave assistance and fluid chemistry.

In the last decade, dozens of aldehyde and ketone compounds with different structures can all be prepared by using lignocellulose[8]. Therefore, how to prepare a compound with a high added value by using renewable small platform molecules effectively also becomes one of hotspots and focuses in the catalysis chemistry research field. It is found through searching that, work of carrying out microwave-assisted addition and reduction reactions on biomass-based aldehyde or ketone and formamide, to selectively convert the biomass-based aldehyde or ketone and the formamide into an amine (particularly primary amine), is rarely reported.

REFERENCES

[1] Kalck, P; Urrutigoity, M. Tandem hydroaminomethylation reaction to synthesize amines from alkenes. Chem. Rev., 2018, 118, 3833-3861.
[2] Jagadeesh, R. V; Murugesan, K.; Alshammari, A. S.; Neumann, H.; Pohl, M.-M.; Radnik, J.; Beller, M. MOF-derived cobalt nanoparticles catalyze a general synthesis of amines. Science, 2017, 358, 326-332.
[3] Froidevaux, V; Negrell, C.; Caillol, S.; Pascault, J. P.; Boutevin, B. Biobased amines: From synthesis to polymers; present and future, Chem. Rev., 2016, 116, 14181-14224.
[4] Liang, G.; Wang, A.; Li, L.; Xu, G.; Yan, N.; Zhang, T. Production of primary amines by reductive amination of biomass-derived aldehydes/ketones. Angew. Chem. Int. Ed., 2017, 56, 3050-3054.
[5] Verduyckt, J.; Coeck, R.; De Vos, D. E. Ru-catalyzed hydrogenation-decarbonylation of amino acids to biobased primary amines. ACS Sustainable Chem. Eng., 2017, 5, 3290-3295.
[6] Klinkenberg, J. L.; Hartwig, J. F. Catalytic organometallic reactions of ammonia. Angew. Chem. Int. Ed., 2011, 50, 86-95.
[7] Bipp, H.; Kieczka, H. "Formamides", Ullmann's Encyclopedia of Industrial Chemistry. Weinheim: Wiley-VCH, 2005.
[8] Liang, G.; Wang, A.; Li, L.; Xu, G.; Yan, N.; Zhang, T. Production of primary amines by reductive amination of biomass-derived aldehydes/ketones. Angew. Chem. Int. Ed., 2017, 56, 3050-3054.

SUMMARY

An objective of the present invention is: for disadvantages, such as high production costs, a long reaction time, and poor selectivity for an amine, of the existing catalysts or catalytic systems, by selecting widely-available and cheap formamide as an amine source, using formic acid as a hydrogen donor, and using biomass aldehyde or ketone as a raw material, to rapidly synthesize a formamide derivative through microwave-assisted heating and in the absence of a solvent and a catalyst, and then remove a formyl group to obtain a primary amine through alcoholysis.

The objective of the present invention is achieved through the following technical solutions:

A rapid synthesis method for a biomass-based amine is provided, including: by using formamide as an amine source, using formic acid as a hydrogen source, and using a biomass aldehyde or ketone compound as a raw material, carrying out a direct addition reaction on the formamide and the aldehyde or ketone compound through microwave-assisted heating and in the absence of a solvent and a catalyst, and then carrying out formic acid reduction to obtain a corresponding formamide derivative; and converting the formamide derivative under the action of a base into a primary amine through an alcoholysis reaction.

In the present invention, the principle of synthesizing a biomass-based amine is: under a heating condition, carrying out an addition reaction (C—N coupling) on the formamide and the aldehyde or ketone compound to generate imine, then reducing the imine into a formamide derivative with hydrogen provided by formic acid, and finally removing a formyl group to obtain an amine through alcoholysis. A reaction formula is as follows:

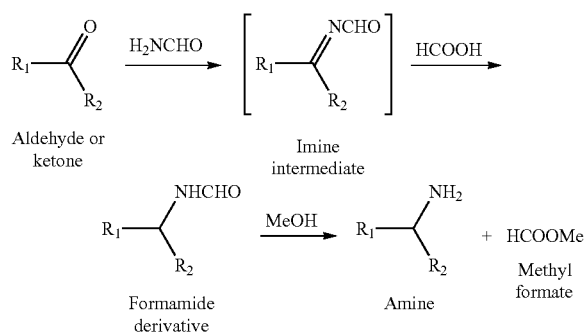

Aldehyde or ketone → Imine intermediate → Formamide derivative → Amine + Methyl formate The formamide derivative is prepared in a microwave reactor, equipped with magnetic stirring. After the microwave reactor is turned on, a specified reaction temperature is set, a reaction system absorbs microwaves and is rapidly heated up to the specified reaction temperature. A microwave power is automatically controlled through frequency conversion with a temperature, and the temperature is controlled by using a thermocouple to maintain the reaction temperature. A preparation process of the formamide derivative is: putting formamide, formic acid, and a biomass aldehyde or ketone compound into a pressure-resistant reaction tube, after the pressure-resistant reaction tube is closed, introducing nitrogen until pressure is 1 to 3 MPa; and placing the pressure-resistant reaction tube into a microwave reactor, and turning on the microwave reactor for a microwave-assisted heating reaction, where the reaction temperature is 160 to 200° C., and a reaction time is 2 to 15 min. Because the system is a high-temperature reaction system, most low-boiling-point components in the system reflux, resulting in a decrease in a probability of contact between low-boiling-point substances and high-boiling-point substances, and further, impact on efficiency and a progress of the reaction. Therefore, before the reaction, nitrogen at 1 to 3 MPa is introduced to suppress gasification of the low-boiling-point compounds, to keep the reaction system in a liquid phase state.

Specifically, a microwave reactor with a microwave frequency of 2.45 GHz and a maximum power of 700 W may be used.

A ratio of amounts of substance of the formamide, the formic acid, and the biomass aldehyde or ketone is 6-15:6-15:2. In the present invention, by controlling excess of the formamide and the formic acid, the reaction is carried out in a positive direction, and a yield of the formamide derivative reaches at least 85%, thereby avoiding generation of a by-product and even a carbonation phenomenon because of excessively low dosages of the formamide and the formic acid, where exceeding dosages requirements for the formamide and the formic acid in the present invention, reaction efficiency is not greatly improved, and there is a large waste of raw materials.

The biomass aldehyde or ketone compound is furfural, 5-methylfurfural, benzaldehyde, veratraldehyde, cinnamaldehyde, glycolaldehyde, propionaldehyde, methyl isobutyl ketone, cyclopentanone, cyclohexanone, or acetophenone. The formamide derivatives corresponding to the foregoing biomass aldehyde or ketone compounds are N-furylmethyl formamide, N-5-methylfurfuryl formamide, N-benzylformamide, N-3,4-dimethoxybenzyl formamide, N-phenylacrylformamide, N-2-hydroxyethyl formamide, N-propylformamide, N-methyl isobutyl formamide, N-cyclopentylformamide, N-cyclohexylformamide, and N-benzyl methyl formamide in sequence. The primary amines corresponding to the foregoing formamide derivatives are 2-furfurylamine, 5-methylfuranethylamine, benzylamine, 3,4-dimethoxybenzylamine, cinnamamide, 2-aminoethanol, propylamine, methylisobutylamine, cyclopentylamine, cyclohexylamine, and benzylmethylamine in sequence.

The alcoholysis reaction includes: solving the formamide derivative in methanol, and under the action of a base, carrying out a reaction at 60 to 100° C. for 2 to 8 h to obtain a primary amine, where a ratio of an amount of substance of the formamide derivative to an amount of substance of the base is 1:1-5, and a ratio of the formamide derivative to the methanol is 1 mol:1 L-3 L; and the base is sodium hydroxide, cesium carbonate, or sodium ethoxide. Methanol is selected for the alcoholysis reaction. Compared with a long-chain alcohol such as ethanol, methanol has a higher reaction activity, and a milder reaction condition.

Beneficial effects of the present invention are as follows:

The method of the present invention promotes direct addition of formamide and an aldehyde or ketone compound by using rapid heating through microwave and in the absence of a solvent and a catalyst, and the formamide and the aldehyde and ketone compound are reduced by using formic acid to obtain a corresponding formamide derivative. Compared with a conventional heating or catalytic system, the reaction system greatly shortens a reaction time, and significantly improves selectivity, where the conversion rate of the biomass aldehyde or ketone compound may reach at least 99%, and a formamide derivative yield may reach 85-99%; the formamide derivative is synthesized into a primary amine through alcoholysis, where a yield may reach 92-99%.

DETAILED DESCRIPTION

The technical solution of the present invention is further described below with reference to examples, but the present invention is not limited by the examples.

Example 1

(1) Microwave-Assisted Catalytic Synthesis of N-Furylmethyl Formamide 2 mmol of furfural, 12 mmol of formamide, and 6 mmol of formic acid were put into a 10 mL pressure-resistant microwave reaction tube, and after the pressure-resistant microwave reaction tube was closed, nitrogen at 2 MPa was introduced. The pressure-resistant microwave reaction tube was placed in a microwave reactor (Shikoku Keisoku Corporation, Japan, model number: SMW-087, microwave frequency: 2.45 GHz, and maximum power: 700 W), the microwave reactor was turned on, a reaction temperature was set to 180° C., a reaction system absorbed microwaves and was rapidly heated up to 180° C., the reaction temperature of the reaction system was controlled by using a thermocouple, microwave-assisted heating and stirring were conducted at this temperature for 3 min, after the reaction was finished, 2 mL of tetrahydrofuran was added, and a furfural conversion rate and an N-furylmethyl formamide yield were measured by using gas chromatography (GC).

(2) Alcoholysis of N-Furylmethyl Formamide 1 mmol of N-furylmethyl formamide was solved into 2 mL of methanol, then 2 mmol of cesium carbonate was added for a reaction at 60° C. for 6 h, and a 2-furfurylamine yield was measured by using GC.

Figure 1:
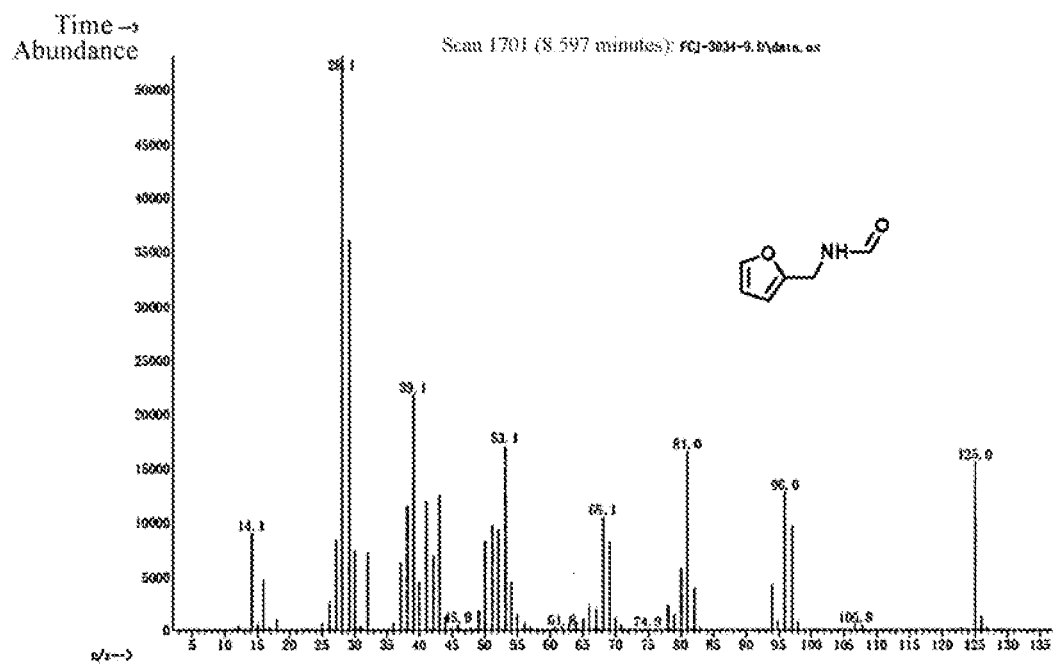
FIG. 1 is a mass spectrum of N-furylmethyl formamide according to Example 1.
Figure 2:
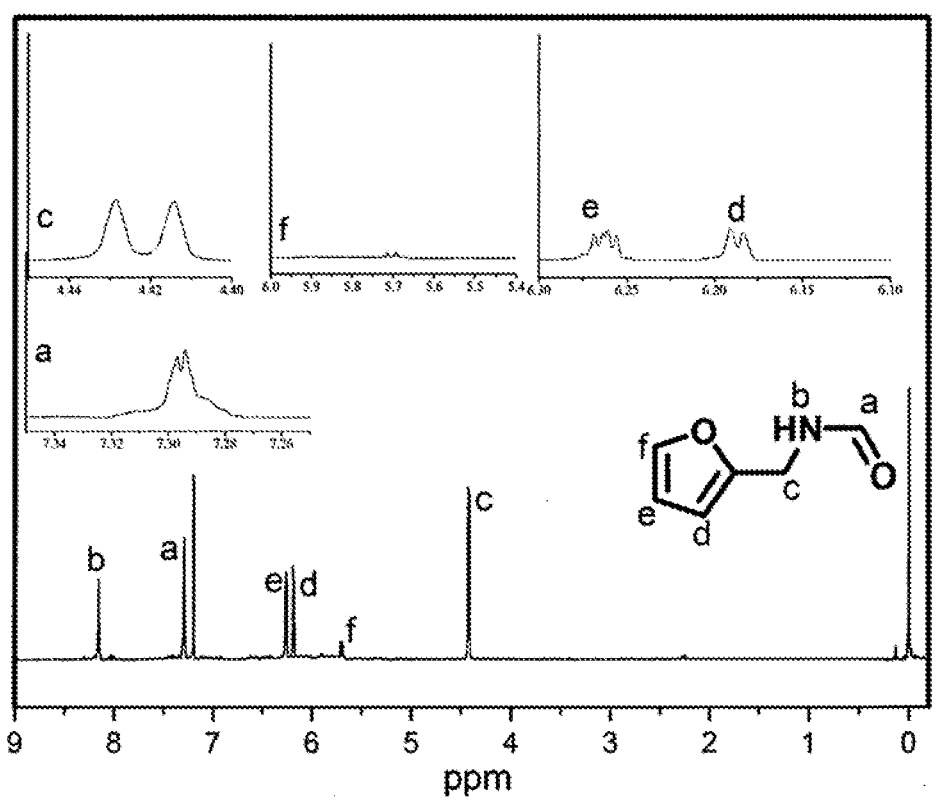
FIG. 2 is a hydrogen spectrum of N-furylmethyl formamide according to Example 1.
Figure 3:
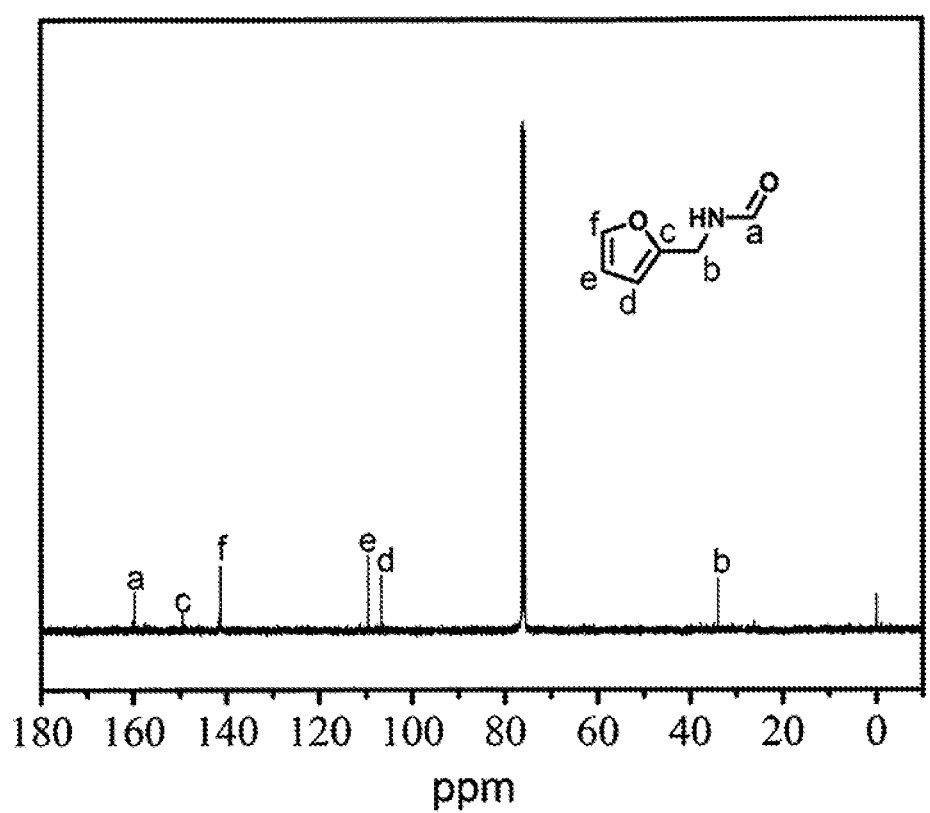
FIG. 3 is a carbon spectrum of N-furylmethyl formamide according to Example 1.

Naphthalene was used as an internal standard for making a standard curve, and the N-furylmethyl formamide yield in the reaction solution was detected to be 98% by using GC. A mass spectrum of the purified N-furylmethyl formamide was shown in FIG. 1, where a molecular ion peak was m/z: 125.0. A hydrogen spectrum and a carbon spectrum were respectively shown FIG. 2 and FIG. 3, where a furfural conversion rate was 100%; and measured based on N-furylmethyl formamide, a 2-furfurylamine yield was 94% (m/z: 97.1).

Comparative Example 1

(1) Catalytic Synthesis of N-Furylmethyl Formamide Through Oil Bath Heating 2 mmol of furfural, 12 mmol of formamide, and 6 mmol of formic acid were put into a 10 mL pressure-resistant reaction tube, and after the pressure-resistant reaction tube was closed, nitrogen at 2 MPa was introduced. Stirring was carried out through oil bath heating under the condition of 180° C. for 60 min, after the reaction was finished, 2 mL of tetrahydrofuran was added to dilute a reaction system, and a furfural conversion rate and an N-furylmethyl formamide yield were measured by using gas chromatography (GC).

Naphthalene was used as an internal standard for making a standard curve, and by using GC, the N-furylmethyl formamide yield in the reaction solution was detected to be 72%, and the furfural conversion rate was detected to be 87%.

Example 2

(1) Microwave-Assisted Catalytic Synthesis of N-Benzylformamide 2 mmol of benzaldehyde, 15 mmol of formamide, and 15 mmol of formic acid were put into a 10 mL pressure-resistant microwave reaction tube, and after the pressure-resistant microwave reaction tube was closed, nitrogen at 1 MPa was introduced; the pressure-resistant microwave reaction tube was placed in a microwave reactor, the microwave reactor was turned on, a reaction temperature was set to 180° C., a reaction system absorbed microwaves and was rapidly heated up to 180° C., the reaction temperature of the reaction system was controlled by using a thermocouple, the reaction system was heated and stirred by using microwaves at 180° C. for 5 min; and after the reaction was finished, 2 mL of tetrahydrofuran was added, and a benzaldehyde conversion rate and an N-benzylformamide yield were measured by using GC.

(2) Alcoholysis of N-Benzylformamide 1 mmol of N-benzylformamide was solved into 2 mL of methanol, then 1 mmol of sodium ethoxide was added for a reaction at 80° C. for 2 h, and a benzylamine yield was measured by using GC.

Naphthalene was used as an internal standard for making a standard curve, and by using GC, the N-benzylformamide yield (m/z: 135.1) in the reaction mixture was detected to be 99%, and the benzaldehyde conversion rate was detected to be 100%; and measured based on N-benzylformamide, the benzylamine yield (m/z: 107.0) was 99%.

Example 3

(1) Microwave-Assisted Catalytic Synthesis of N-Phenylacrylformamide 2 mmol of cinnamaldehyde, 10 mmol of formamide, and 10 mmol of formic acid were put into a 10 mL pressure-resistant microwave reaction tube, and after the pressure-resistant microwave reaction tube was closed, nitrogen at 2 MPa was introduced. The pressure-resistant microwave reaction tube was placed in a microwave reactor, the microwave reactor was turned on, a reaction temperature was set to 200° C., a reaction system absorbed microwaves and was rapidly heated up to 200° C., the reaction temperature of the reaction system was controlled by using a thermocouple, the reaction system was heated and stirred by using microwaves at 200° C. for 2 min, after the reaction was finished, 2 mL, of tetrahydrofuran was added, and a cinnamaldehyde conversion rate and an N-phenylacrylformamide yield were measured by using GC.

(2) Alcoholysis of N-Phenylacrylformamide 1 mmol of N-phenylacrylformamide was solved into 2 mL of methanol, then 1 mmol of sodium hydroxide was added for a reaction at 100° C. for 4 h, and a cinnamamide yield was measured by using GC.

Naphthalene was used as an internal standard for making a standard curve, and by using GC, the N-phenylacrylformamide yield (m/z: 161.0) in the reaction mixture was detected to be 95%, and the cinnamaldehyde conversion rate was detected to be 100%; and measured based on N-phenylacrylformamide, the cinnamamide yield (m/z: 133.1) was 96%.

Example 4

(1) Microwave-Assisted Catalytic Synthesis of N-2-Hydroxyethyl Formamide 2 mmol of 2-glycolaldehyde, 6 mmol of formamide, and 6 mmol of formic acid were put into a 10 mL pressure-resistant microwave reaction tube, and after the pressure-resistant microwave reaction tube was closed, nitrogen at 3 MPa was introduced. The pressure-resistant microwave reaction tube was placed in a microwave reactor, the microwave reactor was turned on, a reaction temperature was set to 160° C., a reaction system absorbed microwaves and was rapidly heated up to 160° C., the reaction temperature of the reaction system was controlled by using a thermocouple, the reaction system was heated and stirred by using microwaves at 160° C. for 15 min, after the reaction was finished, 2 mL of dichloromethane was added, and a 2-glycolaldehyde conversion rate and an N-2-hydroxyethyl formamide yield were measured by using GC.

(2) Alcoholysis of N-2-Hydroxyethyl Formamide 1 mmol of N-2-hydroxyethyl formamide was solved into 1 mL of methanol, then 2 mmol of cesium carbonate was added for a reaction at 60° C. for 8 h, and a yield of obtained 2-aminoethanol was measured by using GC.

Naphthalene was used as an internal standard for making a standard curve, and by using GC, the N-2-hydroxyethyl formamide yield (m/z: 89.1) in the reaction mixture was detected to be 85%, and the 2-glycolaldehyde conversion rate was detected to be 99%; and measured based on N-2-hydroxyethyl formamide, the 2-aminoethanol yield (m/z: 61.0) was 92%.

Example 5

(1) Microwave-Assisted Catalytic Synthesis of N-Methyl Isobutyl Formamide 2 mmol of methyl isobutyl ketone, 15 mmol of formamide, and 10 mmol of formic acid were put into a 10 mL pressure-resistant microwave reaction tube, and after the pressure-resistant microwave reaction tube was closed, nitrogen at 2 MPa was introduced. The pressure-resistant microwave reaction tube was placed in a microwave reactor, the microwave reactor was turned on, a reaction temperature was set to 190° C., a reaction system absorbed microwaves and was rapidly heated up to 190° C., the reaction temperature of the reaction system was controlled by using a thermocouple, the reaction system was heated and stirred by using microwaves at 190° C. for 3 min, after the reaction was finished, 2 mL of tetrahydrofuran was added, and a methyl isobutyl ketone conversion rate and an N-methyl isobutyl formamide yield were measured by using GC.

(2) Alcoholysis of N-Methyl Isobutyl Formamide 1 mmol of N-methyl isobutyl formamide was solved into 2 mL of methanol, then 1 mmol of cesium carbonate was added for a reaction at 80° C. for 5 h, and a yield of obtained methylisobutylamine was measured by using GC.

Naphthalene was used as an internal standard for making a standard curve, and by using GC, the N-methyl isobutyl formamide yield (m/z: 129.0) in the reaction mixture was detected to be 87%, and the methyl isobutyl ketone conversion rate was detected to be 96%; and the methylisobutylamine yield (m/z: 101.1) was 98%.

Example 6

(1) Microwave-Assisted Catalytic Synthesis of N-Cyclopentylformamide 2 mmol of cyclopentanone, 10 mmol of formamide, and 6 mmol of formic acid were put into a 10 mL pressure-resistant microwave reaction tube, and after the pressure-resistant microwave reaction tube was closed, nitrogen at 2 MPa was introduced. The pressure-resistant microwave reaction tube was placed in a microwave reactor, the microwave reactor was turned on, a reaction temperature was set to 200° C., a reaction system absorbed microwaves and was rapidly heated up to 200° C., the reaction temperature of the reaction system was controlled by using a thermocouple, the reaction system was heated and stirred by using microwaves at 200° C. for 2 min, after the reaction was finished, 2 mL of dichloromethane was added, and a cyclopentanone conversion rate and an N-cyclopentylformamide yield were measured by using GC.

(2) Alcoholysis of N-Cyclopentylformamide 1 mmol of N-cyclopentylformamide was solved into 3 mL of methanol, then 2 mmol of cesium carbonate was added for a reaction at 60° C. for 8 h, and a yield of obtained cyclopentylamine was measured by using GC.

Naphthalene was used as an internal standard for making a standard curve, and by using GC, the N-cyclopentylformamide yield (m/z: 113.1) in the reaction mixture was detected to be 98%, and the cyclopentanone conversion rate was detected to be 100%; and the cyclopentylamine yield (m/z: 85.1) was 99%.

Example 7

(1) Microwave-Assisted Catalytic Synthesis of N-Benzyl Methyl Formamide 2 mmol of acetophenone, 6 mmol of formamide, and 12 mmol of formic acid were put into a 10 mL pressure-resistant microwave reaction tube, and after the pressure-resistant microwave reaction tube was closed, nitrogen at 2 MPa was introduced. The pressure-resistant microwave reaction tube was placed in a microwave reactor, the microwave reactor was turned on, a reaction temperature was set to 180° C., a reaction system absorbed microwaves and was rapidly heated up to 180° C., the reaction temperature of the reaction system was controlled by using a thermocouple, the reaction system was heated and stirred by using microwaves at 180° C. for 5 min, after the reaction was finished, 2 mL of tetrahydrofuran was added, and a acetophenone conversion rate and an N-benzyl methyl formamide yield were measured by using GC.

(2) Alcoholysis of N-Benzyl Methyl Formamide 1 mmol of N-benzyl methyl formamide was solved into 2 mL of methanol, then 1 mmol of cesium carbonate was added for a reaction at 80° C. for 3 h, and a yield of obtained 1-phenylethylamine was measured by using GC.

Naphthalene was used as an internal standard for making a standard curve, and by using GC, the N-benzyl methyl formamide yield (m/z: 149.0) in the reaction mixture was detected to be 92%, and the acetophenone conversion rate was detected to be 99%; and the 1-phenylethylamine yield (m/z: 121.1) was 97%.

What is claimed is:

1. A rapid synthesis method for an amine, comprising: by using formamide as an amine source, using formic acid as a hydrogen source, and using an aldehyde or ketone compound as a raw material, carrying out a direct addition reaction on the formamide and the aldehyde or ketone compound through microwave-assisted heating and in the absence of a solvent and a catalyst, and then carrying out formic acid reduction to obtain a corresponding formamide derivative; dissolving the formamide derivative in methanol, and under the action of a base, carrying out a reaction at 60 to 100° C. for 2 to 8 h to obtain the amine, wherein the formamide derivative is prepared in a microwave reactor, a reaction system is an airtight system, nitrogen is introduced before a reaction until pressure is 1 to 3 MPa, a reaction temperature is 160 to 200° C., and a reaction time is 2 to 15 min, a ratio of amounts of substance of the formamide, the formic acid, and the aldehyde or ketone is 6-15:6-15:2, and the aldehyde or ketone compound is furfural, 5-methylfurfural, benzaldehyde, veratraldehyde, cinnamaldehyde, glycolaldehyde, propionaldehyde, methyl isobutyl ketone, cyclopentanone, cyclohexanone, or acetophenone.

2. The rapid synthesis method for an amine according to claim 1, wherein the formamide derivative is N-furylmethyl formamide, N-5-methylfurfuryl formamide, N-benzylformamide, N-3,4-dimethoxybenzyl formamide, N-phenylacrylformamide, N-2-hydroxyethyl formamide, N-propylformamide, N-methyl isobutyl formamide, N-cyclopentylformamide, N-cyclohexylformamide, or N-benzyl methyl formamide.

3. The rapid synthesis method for an amine according to claim 1, wherein a ratio of an amount of substance of the formamide derivative to an amount of substance of the base is 1:1-5, and a ratio of the formamide derivative to the methanol is 1 mol: 1-3 L.

4. The rapid synthesis method for an amine according to claim 1, wherein the base is sodium hydroxide, cesium carbonate, or sodium ethoxide.

5. The rapid synthesis method for an amine according to claim 1, wherein the amine is 2-furfurylamine, 5-methylfuranethylamine, benzylamine, 3,4-dimethoxybenzylamine, cinnamamide, 2-aminoethanol, propylamine, methylisobutylamine, cyclopentylamine, cyclohexylamine, or benzylmethylamine.

\* \* \* \* \*